(12) United States Patent
Cadossi et al.

(10) Patent No.: US 7,004,903 B2
(45) Date of Patent: Feb. 28, 2006

(54) ELECTRONIC SYSTEM FOR DETERMINING THE DENSITY AND STRUCTURE OF BONE TISSUE AND STIMULATING OSTEOGENESIS IN DENTISTRY

(75) Inventors: Ruggero Cadossi, Carpi (IT); Stefania Setti, Carpi (IT); Claudio Bertacchini, Carpi (IT)

(73) Assignee: IGEA S.r.l., (IT)

( * ) Notice: Subject to any disclaimer, the term of this patent is extended or adjusted under 35 U.S.C. 154(b) by 0 days.

(21) Appl. No.: 10/497,788

(22) PCT Filed: Dec. 4, 2002

(86) PCT No.: PCT/IT02/00759

§ 371 (c)(1),
(2), (4) Date: Nov. 22, 2004

(87) PCT Pub. No.: WO03/047451

PCT Pub. Date: Jun. 12, 2003

(65) Prior Publication Data

US 2005/0070797 A1    Mar. 31, 2005

(30) Foreign Application Priority Data

Dec. 5, 2001    (IT)    .................. TO2001A1135

(51) Int. Cl.
*A61B 8/00*    (2006.01)
(52) U.S. Cl. ................. 600/438; 600/439; 600/449
(58) Field of Classification Search ........ 600/437–472; 601/2–4
See application file for complete search history.

(56) References Cited

U.S. PATENT DOCUMENTS

| 5,393,296 | A | * | 2/1995 | Rattner ..................... 601/2 |
| 5,496,256 | A |   | 3/1996 | Bock et al. |
| 6,030,221 | A |   | 2/2000 | Jones et al. |
| 6,652,473 | B1 | * | 11/2003 | Kaufman et al. .......... 601/1 |

FOREIGN PATENT DOCUMENTS

| EP | 0 353 209 | 1/1990 |
| EP | 0 772 999 | 5/1997 |

* cited by examiner

*Primary Examiner*—Ali Imam
(74) *Attorney, Agent, or Firm*—Ostrolenk, Faber, Gerb & Soffen, LLP

(57) ABSTRACT

An electronic system for determining the density and structure of bone tissue and stimulating osteogenesis in dentistry, having a diagnosis system for injecting an ultrasonic signal U(t) into a bone portion and analyzing the ultrasonic signal received after traveling through the bone portion to determine a number of characteristic data items of the signal describing physical and structural characteristics of the bone tissue. The diagnosis system performs a number of measuring steps to determine and memorize a set of characteristic data items describing progress of a bone growth process and/or a bone repair process following extraction of a tooth and/or placement of a dental prosthesis in the bone portion. The system also has an osteogenesis stimulation system for directing an ultrasonic stimulation signal onto the bone portion to promote the bone growth and/or bone repair process.

9 Claims, 4 Drawing Sheets

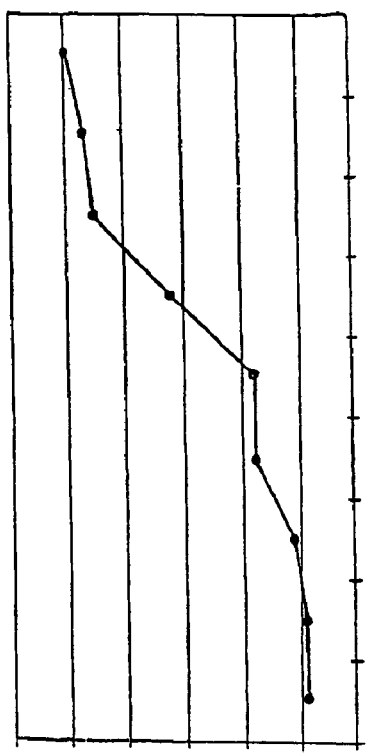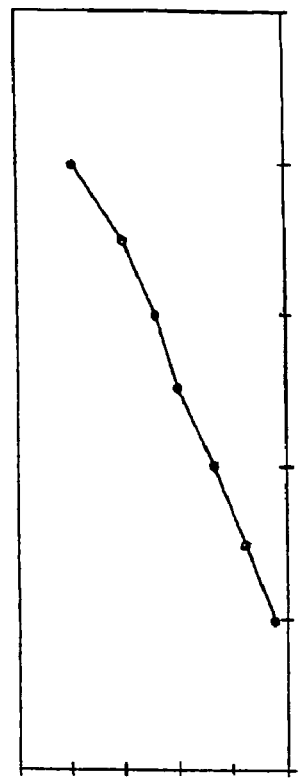
Fig.4a
Fig.4b
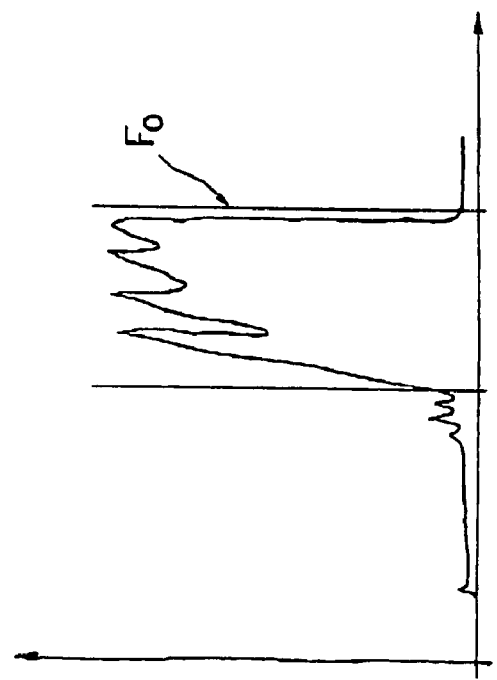
Fig.3 ing device 12 for generating an ultrasonic-frequency signal
ELECTRONIC SYSTEM FOR DETERMINING THE DENSITY AND STRUCTURE OF BONE TISSUE AND STIMULATING OSTEOGENESIS IN DENTISTRY

CROSS REFERENCE TO RELATED APPLICATIONS

The present application is a national stage application under 35 U.S.C. §371 of PCT/IT02/00759 filed 4 Dec. 2002, which claims priority to Italian Application No. TO2001A001135 filed 5 Dec. 2001. The entirety of these applications are hereby incorporated by reference.

TECHNICAL FIELD

The present invention relates to an electronic system for determining the density and structure of bone tissue and stimulating osteogenesis in dentistry.

BACKGROUND ART

As is known, the success of dental implant therapy depends largely on the dimensions and physical-structural characteristics of the bone portion in which the implant is embedded; and the physical-structural characteristics in turn depend on the density, structure and mechanical strength of the bone portion, which must be large enough to accommodate and ensure good mechanical strength of the implant in use.

The success of implant therapy also depends largely on the degree of osteointegration between the outer surface of the implant embedded in the bone and the bone portion itself, which is an essential factor in ensuring stability and efficiency of the implant within the bone, and preventing long-term masticatory pressure on the implant from altering, impairing or even interrupting stable contact between the bone and implant.

To increase the success potential of implant therapy, implants of various forms and structures and various surgical implantation techniques have been devised to select the type of implant and location best suited to the physical and structural characteristics of the bone.

At present, however, operation planning in the sense of selecting the most suitable type of implant and surgical technique is hampered by difficulties in accurately determining the physical and structural characteristics of the bone.

Instrumental diagnosis techniques for determining the physical-structural characteristics of bone tissue are currently based on x-rays, which, however, only provide for a limited amount of data. Moreover, since techniques employing ionizing radiation are known to be potentially harmful, x-ray diagnosis cannot be repeated frequently. EC regulations (DL No. 197 of May 26, 2000) in fact tend towards promoting diagnosis and therapeutic techniques involving no ionizing radiation.

Therapeutic bone reconstruction techniques have been devised employing bone (or bone-substitute) grafts and/or membranes forming a substrate by which to regenerate the bone tissue, but are extremely slow (extending over months), and the degree of bone regeneration achieved using known techniques is somewhat variable and difficult to determine.

A demand therefore exists for a system involving no ionizing radiation, which provides a clear indication of the physical-structural characteristics of bone tissue, and which also provides for controlling and promoting bone reconstruction and regeneration.

DISCLOSURE OF THE INVENTION

According to the present invention, there is provided an electronic system for determining the density and structure of bone tissue and stimulating osteogenesis in dentistry, as claimed in claim 1.

BRIEF DESCRIPTION OF THE DRAWINGS

A preferred, non-limiting embodiment of the invention will be described by way of example with reference to the accompanying drawings, in which:

FIG. 3 shows the waveform of a signal analyzed by the FIG. 1 system;

FIGS. 4a and 4b show curves processed by the system according to the present invention.

BEST MODE FOR CARRYING OUT THE INVENTION

Figure 1:
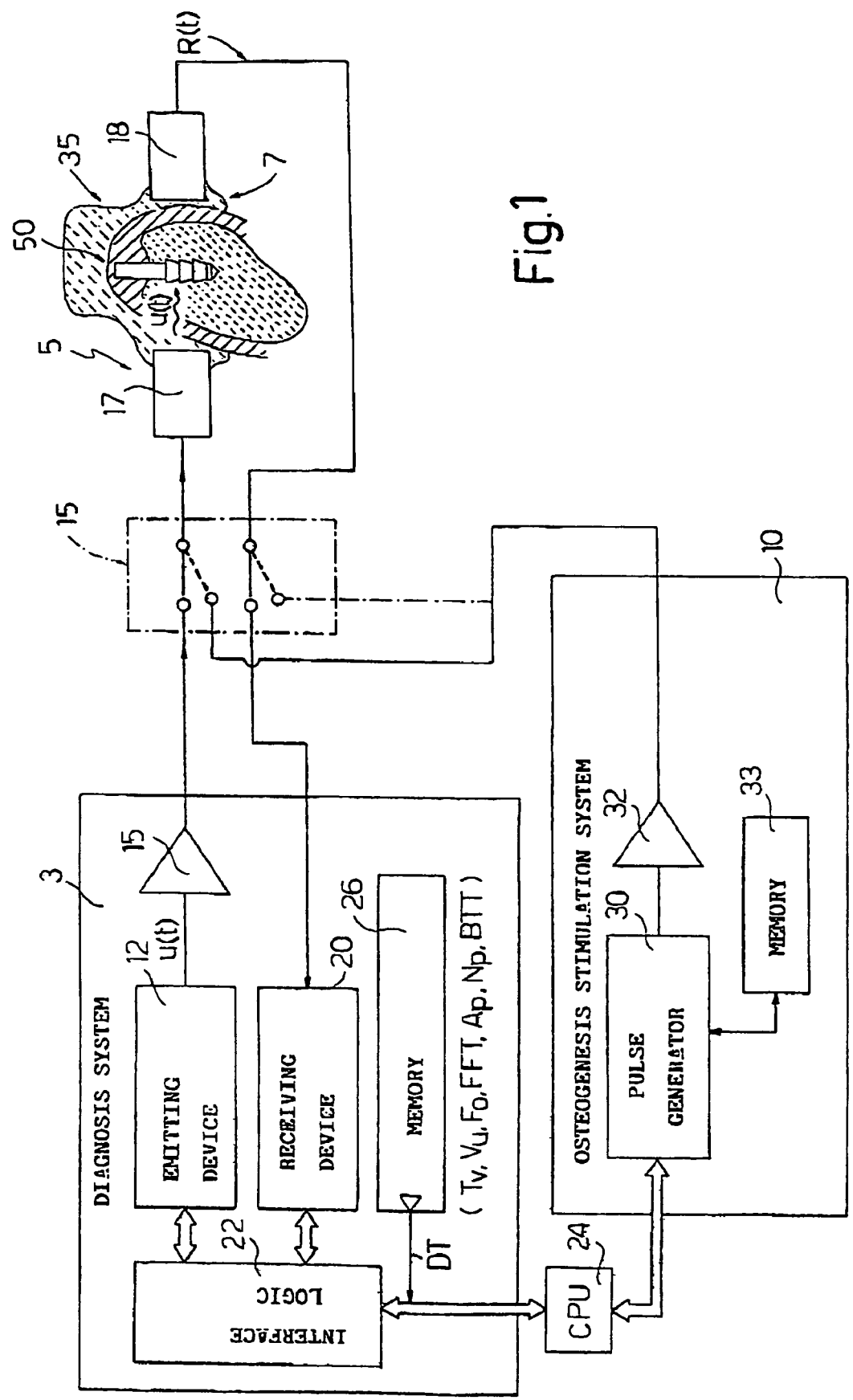
FIG. 1 shows, schematically, an electronic system for determining the density and structure of bone tissue and stimulating osteogenesis in dentistry, in accordance with the teachings of the present invention.
Figure 2A:
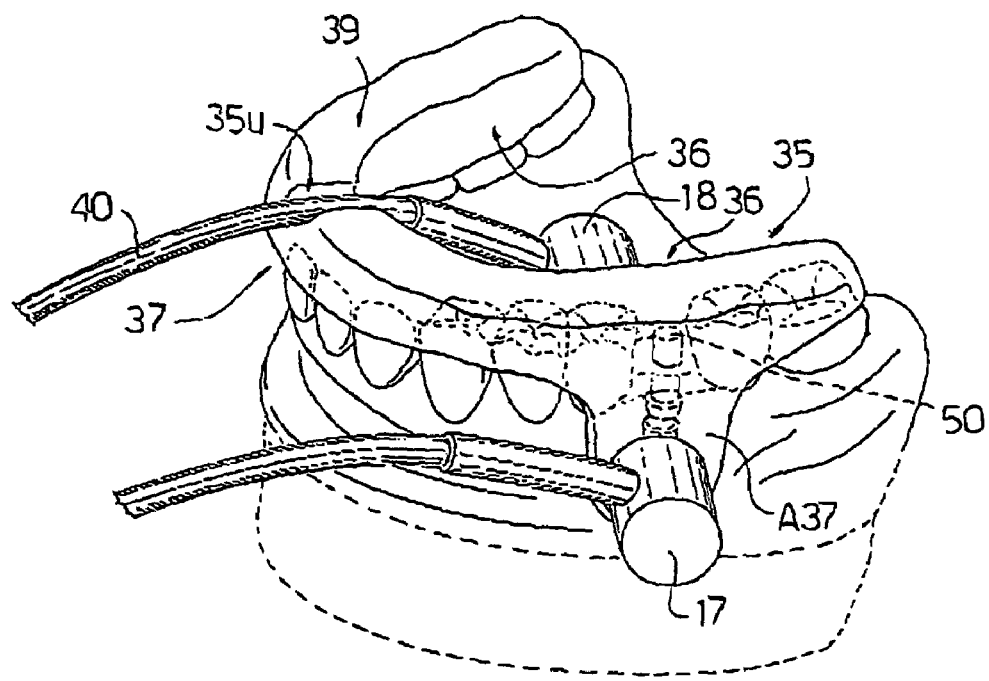
FIG. 2a shows a top view in perspective of a supporting structure for a transducer device forming part of the FIG. 1 system.
Figure 2B:
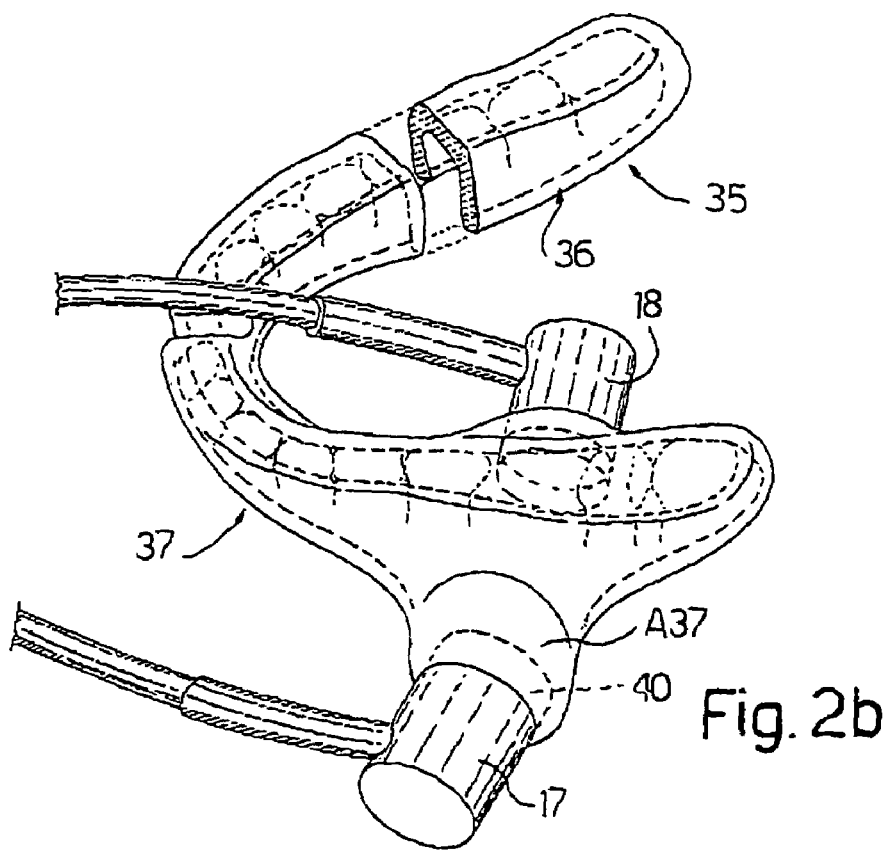
FIG. 2b shows a bottom view in perspective of the FIG. 2a supporting structure.
Figure 2C:
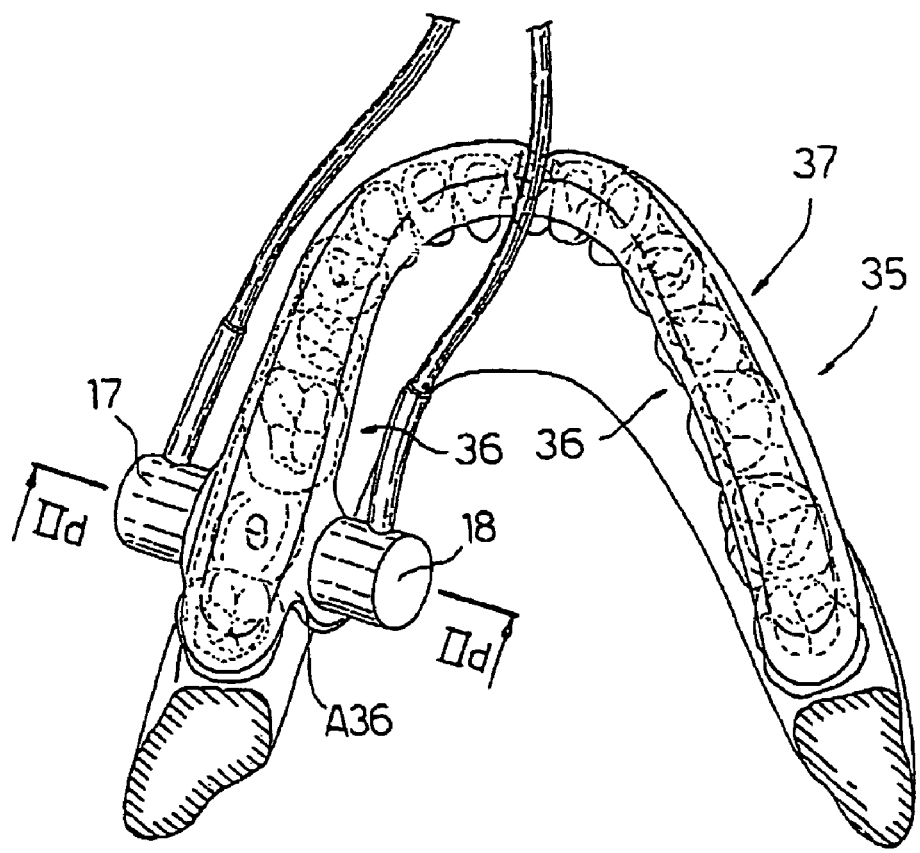
FIG. 2c shows a rear view in perspective of the FIG. 2a, 2b supporting structure.
Figure 2D:
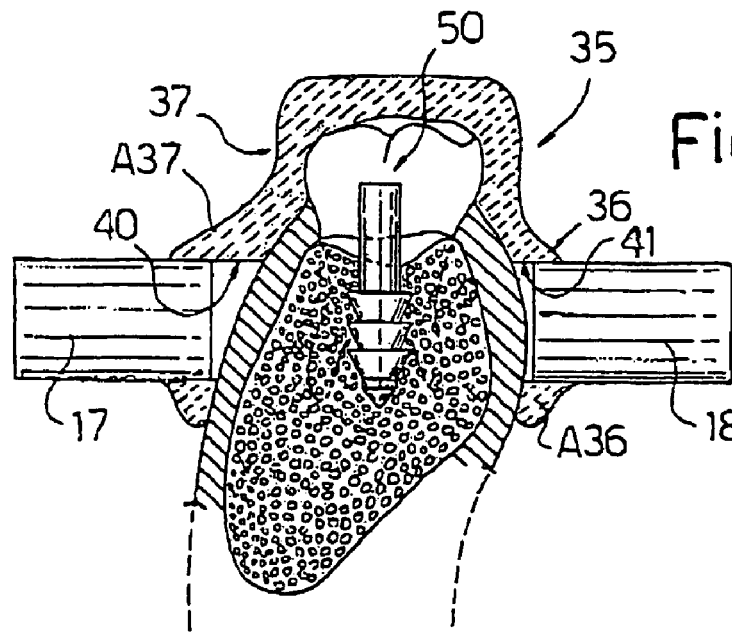
FIG. 2d shows a section of the supporting structure along line IId—IId in FIG. 2c.

Number 1 in FIG. 1 indicates as a whole an electronic system for determining the density and structure of bone tissue and stimulating osteogenesis in dentistry.

System 1 comprises a diagnosis system 3 (shown schematically) which cooperates with a transducer device 5 connectable to a bone tissue portion 7 (shown schematically) and for detecting and memorizing data DT representing physical and structural characteristics of bone tissue portion 7.

System 1 also comprises an osteogenesis stimulation system 10 cooperating with transducer device 5 and for activating and sustaining a process of growth and/or repair of bone tissue portion 7, in particular following a dental operation.

In the embodiment shown, diagnosis system 3 and osteogenesis stimulation system 10 are shown as forming part of one device and therefore having one transducer 5.

Diagnosis system 3 and osteogenesis stimulation system 10, however, may obviously form part of different (in particular, two portable) devices, each having a respective transducer device.

More specifically, diagnosis system 3 comprises an emitting device 12 for generating an ultrasonic-frequency signal $u(t)$, in particular an emitting device for generating, for example, a square-wave signal of 1.25 to 1.5 MHz frequency, 102.4 µs repetition rate, and 24 Vpp amplitude.

Signal $u(t)$ is amplified by an amplifying device 13 and sent, via a switch device 15 in a first operating position, to a first transducer (in particular, a piezoelectric transducer) 17 of device 5 to generate and direct an ultrasonic signal U(t) onto bone tissue portion 7.

Device 5 also comprises a second transducer 18 located on the opposite side of bone tissue portion 7 to transducer 17, and for receiving the portion of ultrasonic signal U(t) traveling through bone tissue portion 7.

Second transducer 18 generates a response signal R(t) which, after traveling through switch device 15 in the first position, is acquired by a signal receiving device 20.

Emitting device 12 and signal receiving device 20 interact, via interface logic 22, with a CPU 24, which thus receives information concerning the emission times and waveform of ultrasonic signal U(t) injected into bone tissue portion 7, and the reception times and waveform of the response signal R(t) received after traveling through the bone tissue portion.

More specifically, CPU 24 performs known analysis operations, and in particular:

calculates the time Tv (transit time) taken by the ultrasonic signal to travel through bone tissue portion 7;

calculates ultrasound transmission speed Vu according to the equation d/Tv, where d is the distance between transducers 17, 18, i.e. the thickness of bone tissue portion 7;

examines the received signal waveform (FIG. 3), and defines on the waveform an observation window Fo delimiting the portion of the signal which has actually traveled through the bone tissue, so as to eliminate the effect of the signal transmitted through the soft tissue surrounding the bone tissue (this can be done using the operations described in IGEA S.r.l. European Patent EP-663.182);

performs a Fourier transform (in particular, a fast Fourier transform FFT) of the received signal waveform;

determines the amplitude Ap of the most significant peak in the received signal waveform;

determines the number of peaks Np in the received signal; and calculates BTT (bone transmission time).

All the results from analyzing the received ultrasonic signal are memorized in a memory 26; and, for each analysis, the observation instant (or time interval) Tanalysis in which the analysis was made is determined and memorized.

Diagnosis system 3 therefore provides for analyzing the bone tissue, and for determining and memorizing a number of data items DT (Tv, Vu, Fo, Ap, Np, FFT, BTT) describing the physical-structural characteristics of the bone tissue.

Osteogenesis stimulation system 10 comprises an ultrasonic pulse generating device 30 for generating trains of ultrasonic pulses of predetermined frequency (e.g. 1.5 MHz), predetermined amplitude (e.g. 200 $\mu$s), and a predetermined repeat interval (e.g. 1 KHz). The power of the generated signal preferably ranges between 30 mW/cm$^2$ and 50 mW/cm$^2$.

The pulses are amplified by an amplifier 32 and sent, via switch device 15 in a second operating position, to one (or both) of transducers 17, 18 to generate and direct an ultrasonic signal onto bone tissue portion 7.

Pulse generating device 30 operates under control of CPU 24, and cooperates with a dedicated memory 33 (or with memory 26) to memorize characteristic parameters (frequency, pulse train amplitude, repetition rate) of the generated ultrasonic signal, and the time interval Tapp in which the signal was applied to bone tissue portion 7.

FIGS. 2a, 2b, 2c and 2d show a detailed example of the mechanical structure of transducer device 5. It should be pointed out that bone tissue portion 7 is located on a bone structure supporting a number of teeth, i.e. on the upper or lower jaw.

Transducer device 5 (FIGS. 2a–2d) comprises a supporting structure 35 shaped to mate with, and to enclose the teeth supported by, the bone structure. More specifically, supporting structure 35 is defined by a roughly U-shaped body made of rigid plastic material, e.g. polymethacrylate or polymethyl methacrylate, and having a number of inner cavities extending along a U-shaped path and for housing respective teeth forming part of a dental arch. Supporting structure 35 may obviously differ from the one shown, and comprise, for example, only a short curved portion mating with a small number of (e.g. two or three) teeth on the dental arch.

Supporting structure 35 is "custom made" for each patient by taking an impression, in known manner, of the dental arch concerned, making a plaster model reproducing the bone structure complete with the gum and teeth, and then shaping supporting structure 35 on the plaster model, so that the supporting structure is complementary in shape to the plaster model and therefore the dental arch of the patient.

More specifically, U-shaped supporting structure 35 is defined, among other things, by an inner wall 36 positioned, in use, facing the patient's tongue, and by an outer wall 37 positioned, in use, facing a vestibular side of the mouth.

Outer wall 37 has a short appendix A37 in which is formed a seat 40 for stably housing an end portion of first transducer 17; and inner wall 36 has a short appendix A36 in which is formed a seat 41 facing seat 40 and for stably housing an end portion of second transducer 18. Transducers 17, 18 are thus both carried by supporting structure 35, and are located facing each other in fixed stable positions with respect to the supporting structure.

Supporting structure 35 has a seat 35$u$ (FIG. 2a) formed in a central portion of a wall 39 crosswise to walls 36, 37, and for the passage of the cable 40 connected to transducer 18.

When supporting structure 35 is fitted to the teeth, no relative movement is permitted between the parts, so that transducers 17, 18 are located in predetermined positions with respect to the bone structure. More specifically, both transducers 17, 18 face the same bone tissue portion 7 through which the ultrasound travels.

System 1 is used for patient analysis and conditioning, in particular a patient requiring extraction and replacement of one or more teeth with a dental implant.

A "custom made" supporting structure of the type described above is made for the patient, with transducers 17, 18 located at the bone tissue portion 7 containing the tooth/teeth for extraction, or at a bone tissue portion for reconstruction.

The tooth/teeth is/are then extracted, and supporting structure 35 is applied to determine, by means of diagnosis system 3 (with switch device 15 in the first operating position), the characteristics of bone tissue portion 7 from which the tooth/teeth has/have been extracted. Even if no extraction is performed, the physical and structural characteristics of the bone tissue are still assessed. That is, a number of data items DT describing the physical and structural characteristics of the bone tissue are determined.

Assessments are made at intervals (e.g. weekly or every two weeks) to compile a set of data items DT relating to different successive times DTt1, DTt2, . . . DTti, . . . DTtn.

Data items DTt1, DTt2, . . . DTti, . . . DTtn may also be represented graphically.

For example, a speed-time pattern (FIG. 4a) may be monitored, memorized and plotted to show repair of the bone, i.e. regeneration of the bone following extraction of a tooth, in which speed increases up to a point at which it eventually levels off.

A speed-time pattern (FIG. 4b) may also be monitored, memorized and plotted to show repair of the bone following insertion of the implant.

Bone growth not preceded by any dental operation may also be monitored.

Operations may also be performed to stimulate bone growth by setting switch device 15 to the second operating position, and subjecting bone tissue portion 7 (using one or both transducers) to trains of ultrasonic pulses at successive times (e.g. every day).

The same system thus provides for two processes:
 a measuring process, by which to determine, at successive times, data items DT representing the variation over time in the physical and structural characteristics of the bone tissue, particularly following tooth extraction, and therefore growth and/or repair of the bone; and
 a curative process by which to promote growth/repair of bone tissue portion 7, particularly following a tooth extraction.

When data items DT show sufficient growth or repair of the bone tissue, as indicated by data items DT reaching substantially stable values, a hole (or number of holes) is formed in bone tissue portion 7, and the implant 50 is inserted.

The operations described above are repeated by reapplying supporting structure 35 (possibly modified slightly so as not to interfere with implant 50) to determine, by means of diagnosis system 3 (with switch device 15 in the first operating position), the characteristics of bone tissue portion 7 into which implant 50 is embedded. That is, a number of data items DT representing the physical and structural characteristics of the bone tissue incorporating implant 50 are determined.

Assessments are made at intervals (e.g. weekly or every two weeks) to compile a set of data items DT relative to different successive times DTt1, DTt2, . . . DTti, . . . DTtn.

Operations may also be performed to stimulate bone growth (osteointegration) and consolidation of the bone and implant 50 by setting switch device 15 to the second operating position, and subjecting bone tissue portion 7 to trains of ultrasonic pulses at successive times (e.g. every day for 20–40 minutes).

As before, the same system thus provides for two processes:
 a measuring process, by which to determine, at successive times, data items DT representing the variation over time in the physical and structural characteristics of the bone tissue following insertion of implant 50; and
 a curative process by which to promote reconstruction of bone tissue portion 7 and consolidation of the bone tissue and implant 50.

The advantages of the system according to the present invention will be clear from the foregoing description. By means of diagnosis system 3, it provides for accurately determining the physical and structural characteristics of the bone tissue into which the implant is embedded; a noninvasive diagnosis system is employed; the most suitable implant and surgical implantation technique can be selected; bone growth can be promoted and, following tooth extraction, bone repair can be monitored continuously, and numerous assessments made to monitor the healing process and determine complete healing of the bone; and, during the above diagnosis process, reconstruction of the bone can be promoted by stimulation system 10.

Moreover, once the implant is inserted, the physical and structural characteristics of the bone containing the implant can be determined immediately; repair of the bone containing the implant can be monitored; and osteointegration of the implant is promoted by stimulation system 10.

Finally, supporting structure 35 provides for accurate repeat positioning of transducers 17, 18 with respect to bone tissue portion 7, thus enabling repeatable measurements at successive assessments/applications.

A device (e.g. a potentiometric device, not shown) may also be provided for measuring distance d between transducers 17, 18, and supplying the value of distance d to CPU 24 to calculate ultrasound transmission speed Vu.

What is claimed is:

1. An electronic system for determining the density and structure of bone tissue and stimulating osteogenesis in dentistry,
 characterized by comprising:
  a diagnosis system (3) comprising an ultrasound emitting device (12) cooperating with a first transducer (17) to send an ultrasonic signal U(t) to a bone portion (7), and a receiving device (20) for receiving the ultrasonic signal picked up by a second transducer (18) after traveling through said bone portion; said diagnosis system also comprising a signal analyzing device (22) cooperating with said receiving device (20) to determine a number of characteristic data items DT (Tv, Vu, Fo, Ap, Np, FFT, BTT) describing physical and structural characteristics of the bone tissue;
  said diagnosis system (3) operating under the control of control means (24) to perform a number of measuring steps to determine and memorize (26) a set of characteristic data items (DT) relating to different successive times; said set of characteristic data items describing the progress of a bone growth process or a bone repair process following extraction of a tooth and/or placement of a dental prosthesis in said bone portion; and
  an osteogenesis stimulation system (10) comprising an ultrasonic pulse generating device (30) for directing an ultrasonic stimulation signal onto said bone portion (7) to promote the bone growth and/or bone repair process.

2. An electronic system for determining the density and structure of bone tissue and stimulating osteogenesis in dentistry,
 characterized by comprising:
  a diagnosis system (3) comprising an ultrasound emitting device (12) cooperating with a first transducer (17) to send an ultrasonic signal U(t) to a bone portion (7), and a receiving device (20) for receiving the ultrasonic signal picked up by a second transducer (18) after traveling through said bone portion; said diagnosis system also comprising a signal analyzing device (22) cooperating with said receiving device (20) to determine a number of characteristic data items DT (Tv, Vu, Fo, Ap, Np, FFT, BTT) describing physical and structural characteristics of the bone tissue;
  said diagnosis system (3) operating under the control of control means (24) to perform a number of measuring steps to determine and memorize (26) a set of characteristic data items (DT) relating to different successive times; said set of characteristic data items describing the progress of a bone growth process or a bone repair process following extraction of a tooth and/or placement of a dental prosthesis in said bone portion; and an osteogenesis stimulation system (10) comprising an ultrasonic pulse generating device (30) for directing an ultrasonic stimulation signal onto said bone portion (7) to promote the bone growth and/or bone repair process, wherein said osteogenesis stimulation system (10) comprises memory means (33) for memorizing at least one of the following quantities:

characteristic parameters of said ultrasonic stimulation signal; and the time interval (Tapp) in which said ultrasonic stimulation signal is applied to said bone portion (7).

3. A system as claimed in claim 2, wherein said ultrasound emitting device (12) generates a wave, in particular a square wave, with a frequency of 1.25 to 1.5 Mhz.

4. A system as claimed in claim 2, wherein said ultrasonic pulse generating device (30) generates trains of ultrasonic pulses with a frequency close to 1.5 MHz, a predetermined amplitude of substantially 200 μs, and a predetermined repeat interval of about 1 KHz.

5. An electronic system for determining the density and structure of bone tissue and stimulating osteogenesis in dentistry, characterized by comprising:

a diagnosis system (3) comprising an ultrasound emitting device (12) cooperating with a first transducer (17) to send an ultrasonic signal U(t) to a bone portion (7), and a receiving device (20) for receiving the ultrasonic signal picked up by a second transducer (18) after traveling through said bone portion; said diagnosis system also comprising a signal analyzing device (22) cooperating with said receiving device (20) to determine a number of characteristic data items DT (Tv, Vu, Fo, Ap, Np, FFT, BTT) describing physical and structural characteristics of the bone tissue;

said diagnosis system (3) operating under the control of control means (24) to perform a number of measuring steps to determine and memorize (26) a set of characteristic data items (DT) relating to different successive times; said set of characteristic data items describing the progress of a bone growth process or a bone repair process following extraction of a tooth and/or placement of a dental prosthesis in said bone portion; and an osteogenesis stimulation system (10) comprising an ultrasonic pulse generating device (30) for directing an ultrasonic stimulation signal onto said bone portion (7) to promote the bone growth and/or bone repair process, wherein said signal analyzing device (22) comprises electronic means for performing at least one of the following operations:

calculating the transit time (Tv) taken by the ultrasonic signal to travel through the bone portion (7);

calculating ultrasound transmission speed (Vu) through said bone portion;

examining the waveform of the signal received from said second transducer (18), and defining on the waveform an observation window (Fo) delimiting the portion of the signal which has actually traveled through the bone tissue, so as to eliminate the effect of the signal transmitted through the soft tissue surrounding the bone tissue;

performing a Fourier transform, in particular a fast Fourier transform FFT, of the waveform of the received signal;

determining the amplitude Ap of the most significant peak in the waveform of the received signal; and determining the number of peaks Np in the received signal.

6. An electronic system for determining the density and structure of bone tissue and stimulating osteogenesis in dentistry, characterized by comprising:

a diagnosis system (3) comprising an ultrasound emitting device (12) cooperating with a first transducer (17) to send an ultrasonic signal U(t) to a bone portion (7), and a receiving device (20) for receiving the ultrasonic signal picked up by a second transducer (18) after traveling through said bone portion; said diagnosis system also comprising a signal analyzing device (22) cooperating with said receiving device (20) to determine a number of characteristic data items DT (Tv, Vu, Fo, Ap, Np, FFT, BTT) describing physical and structural characteristics of the bone tissue;

said diagnosis system (3) operating under the control of control means (24) to perform a number of measuring steps to determine and memorize (26) a set of characteristic data items (DT) relating to different successive times; said set of characteristic data items describing the progress of a bone growth process or a bone repair process following extraction of a tooth and/or placement of a dental prosthesis in said bone portion; and an osteogenesis stimulation system (10) comprising an ultrasonic pulse generating device (30) for directing an ultrasonic stimulation signal onto said bone portion (7) to promote the bone growth and/or bone repair process, wherein a supporting structure (35) is provided, which is shaped to match the outline of at least part of the bone portion, and to enclose at least one tooth carried by the bone structure;

said supporting structure supporting said first transducer and said second transducer facing each other and in fixed positions with respect to said supporting structure.

7. A system as claimed in claim 6, wherein said supporting structure (35) is defined by a substantially U-shaped body of substantially rigid material; said body of substantially rigid material having a number of inner cavities extending along a U-shaped path and for housing respective teeth.

8. A system as claimed in claim 7, wherein the supporting structure is custom made for a patient by taking an impression of the dental arch concerned, and then making a model of inert material reproducing the bone structure complete with the gum and teeth; said supporting structure being made on said model of inert material so that the supporting structure (35) is complementary to the model.

9. A system as claimed in claim 7, wherein the U-shaped supporting structure (35) is defined, among other things, by an inner wall (36) which is positioned, in use, facing a patient's tongue, and by an outer wall (37) which is positioned, in use, facing a vestibular side of the mouth;

said outer wall (37) having a first seat (40) for stably housing an end portion of the first transducer (17), and the inner wall (36) having a second seat (41) facing the first seat (40) and for stably housing an end portion of said second transducer (18).

* * * * *